United States Patent
Park et al.

(10) Patent No.: US 11,826,122 B2
(45) Date of Patent: *Nov. 28, 2023

(54) METHOD AND SYSTEM FOR MANAGING ENERGY TRANSFER BETWEEN A PASSIVE IMPLANTED MEDICAL DEVICE AND EXTERNAL DEVICE

(71) Applicant: ST. JUDE MEDICAL LUXEMBOURG HOLDINGS II S.A.R.L. ("SJM LUX II"), Luxembourg (LU)

(72) Inventors: Jin Woo Park, Duluth, TX (US); Michael Fonseca, Powder Springs, GA (US); William D. Barrett, Tucker, GA (US); Philip M. FitzSimons, Lilburn, GA (US)

(73) Assignee: ST. JUDE MEDICAL LUXEMBOURG HOLDINGS II S.A.R.L. (, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 17/958,464

(22) Filed: Oct. 3, 2022

(65) Prior Publication Data

US 2023/0025231 A1    Jan. 26, 2023

Related U.S. Application Data

(63) Continuation of application No. 16/452,279, filed on Jun. 25, 2019, now Pat. No. 11,490,813.

(51) Int. Cl.
*H02J 50/90* (2016.01)
*A61B 5/00* (2006.01)
(Continued)

(52) U.S. Cl.
CPC .......... *A61B 5/0031* (2013.01); *H01Q 1/244* (2013.01); *H02J 7/00034* (2020.01); *H02J 50/12* (2016.02);
(Continued)

(58) Field of Classification Search
CPC ..................................... H02J 50/90
(Continued)

(56) References Cited

U.S. PATENT DOCUMENTS

2008/0300660 A1* 12/2008 John .................. A61N 1/37252
607/61
2011/0193688 A1* 8/2011 Forsell .................... H02J 50/80
320/108

(Continued)

*Primary Examiner* — Edward Tso
*Assistant Examiner* — Ahmed H Omar
(74) *Attorney, Agent, or Firm* — THE SMALL PATENT LAW GROUP LLC; Dean D. Small

(57) ABSTRACT

A computer implemented method, system and device are provided. The method transmits an energizing signal from an external antenna, coupled to a local external device (LED), to an implanted antenna of a passive implanted medical device (PIMD). The energizing signal is transmitted while the external antenna is at first and second positions. The method receives, at the external antenna, first and second energy transfer characteristic (ETC) values associated with the first and second positions, respectively. The method is under control of one or more processors configured with program instructions. The method analyzes the first and second ETC values to determine a difference therebetween. The method provides an energy transfer level (ETL) indicator based on the difference between the first and second ETC values. The ETL indicator provides feedback regarding a degree of energy transfer associated with at least one of the first and second positions.

22 Claims, 7 Drawing Sheets

(51) Int. Cl.
  *H01Q 1/24*   (2006.01)
  *H02J 50/12*  (2016.01)
  *H02J 50/80*  (2016.01)
  *H02J 7/00*   (2006.01)
  *H02J 50/40*  (2016.01)

(52) U.S. Cl.
  CPC .............. *H02J 50/40* (2016.02); *H02J 50/80* (2016.02); *H02J 50/90* (2016.02); *A61B 2560/0219* (2013.01)

(58) Field of Classification Search
  USPC ........................................................ 320/108
  See application file for complete search history.

(56) References Cited

U.S. PATENT DOCUMENTS

| | | |
|---|---|---|
| 2012/0262108 A1 | 10/2012 | Olson et al. |
| 2016/0109564 A1 | 4/2016 | Sieber et al. |
| 2018/0247095 A1 | 8/2018 | Sundaram et al. |
| 2019/0009097 A1* | 1/2019 | Hartley .................. H02J 50/90 |

* cited by examiner

METHOD AND SYSTEM FOR MANAGING ENERGY TRANSFER BETWEEN A PASSIVE IMPLANTED MEDICAL DEVICE AND EXTERNAL DEVICE

RELATED APPLICATION

The present application is a continuation application of, and claims priority to, U.S. application Ser. No. 16/452,279, Titled "METHOD AND SYSTEM FOR MANAGING ENERGY TRANSFER BETWEEN A PASSIVE IMPLANTED MEDICAL DEVICE AND EXTERNAL DEVICE" which was filed on 25 Jun. 2019, the complete subject matter of which is expressly incorporated herein by reference in its entirety.

BACKGROUND

Today, passive implantable medical devices (PIMDs) and local external devices exist that utilize a wireless interface to communicate with one another and monitor physical conditions within a body. PIMDs require power from an external source for operation. For example, a PIMD may be a passive implantable sensor. The PIMD is implanted at a select location within a body and used to detect a physiological parameter of interest. The local external device supplies power to, and detects signals from, the passive implantable sensor. The detected signals are indicative of the physiological parameter of interest. Currently, wireless interface transfers energy between an external antenna of the local external device and an implanted antenna incorporated into the PIMD in order to provide power to and receive signals from the PIMD.

However, conventional interfaces experience certain limitations. During energy transfer a clinician holds/positions the external antenna at one or more positions against or near an external surface of the patient. The clinician knows a general position of the implanted antenna but does not know an exact position and orientation of the implanted antenna. The exact location and orientation of the PIMD, and thus the implanted antenna, cannot be seen by a user of the local external device. Therefore, the external antenna may be held at various alignments relative to the implanted antenna. The relative position of the external antenna and the implanted antenna impacts a degree of energy transfer between the external antenna and the implanted antenna. Alignment of the external antenna relative to the implanted antenna remains a difficulty when implementing wireless interfaces for PIMDs. Difficulty in aligning the external antenna and the implanted antenna may lead to insufficient power to initiate operation of the PIMD and poor communications signal strength.

Wireless interfaces are frequently used by clinicians and patients in order to monitor and manage disease states. One factor in ensuring successful monitoring and management of a disease state using a wireless interface is ensuring that a user can operate the system easily and correctly.

Accordingly, a need remains for methods and systems to guide positioning of an external antenna coupled to a local external device relative to an implanted antenna of a PIMD in order to manage the degree of energy transfer between the external antenna and the implanted antenna.

SUMMARY

In accordance with embodiments herein, a computer implemented method is provided. The method transmits an energizing signal from an external antenna, coupled to a local external device (LED), to an implanted antenna of a passive implanted medical device (PIMD). The energizing signal is transmitted while the external antenna is at first and second positions. The method receives, at the external antenna, first and second energy transfer characteristic (ETC) values associated with the first and second positions, respectively. The method is under control of one or more processors configured with program instructions. The method analyzes the first and second ETC values to determine a difference therebetween. The method provides an energy transfer level (ETL) indicator based on the difference between the first and second ETC values. The ETL indicator provides feedback regarding a degree of energy transfer associated with at least one of the first and second positions.

Optionally, the providing the ETL indicator may include a change from a first ETL indicator associated with the first ETC value to a second ETL indicator associated with the second ETC value. The change may indicate a change in the degree of energy transfer when moving the external antenna from the first position to the second position.

The change in the degree of energy transfer may represent an increase or a decrease in the degree of energy transfer. The degree of energy transfer may increase when the analyzing determines that the first ETC value is greater than the second ETC value. The degree of energy transfer may decrease when the analyzing determines that the first ETC value is less than the second ETC value.

Optionally, the first and second positions may correspond to current and previous positions, respectively, of the external antenna with respect to the implanted antenna. The providing may include changing the ETL indicator to indicate a decrease in the degree of energy transfer when the current position is associated with a first ETC value that may be lower than the second ETC value associated with the previous position. The providing may include changing the ETL indicator to indicate an increase in the degree of energy transfer when the current position is associated with a first ETC value that may be greater than the second ETC value associated with the previous position. The method may obtain movement data indicative of movement of the external antenna relative to a reference. The providing may include changing the ETL indicator based on the movement data.

Optionally, the analyzing step may comprise analyzing the first and second ETC values in combination with the movement data to determine whether a change between the first and second ETC values was accompanied by movement of the external antenna. The analyzing may comprise estimating a current level of available power of the PIMD based on at least a predetermined value of power consumption of the PIMD for at least one PIMD operation and a change in the first ETC value over the second ETC value over a select time interval. The estimating may comprise accounting for power calculation noise originating from moving the external antenna from the first position to the second position. The method may initiate a select PIMD operation if the current level of available power of the PIMD is above a threshold value for the select PIMD operation. The method may delay a select PIMD operation if the current level of available power of the PIMD is below a threshold value for the select PIMD operation. The first position and the second position may be the same.

In accordance with embodiments herein, a system is provided. The system includes an external antenna coupled to a local external device (LED). The external antenna is configured to transmit an energizing signal to an implanted antenna of a passive implanted medical device (PIMD). The energizing signal is transmitted while the external antenna is at first and second positions and receives first and second energy transfer characteristic (ETC) values associated with the first and second positions. The system includes at least one LED processor and a LED memory coupled to the at least one LED processor. The memory stores program instructions. The program instructions are executable by the at least one processor for analyzing the first and second ETC values to determine a difference therebetween and providing an energy transfer level (ETL) indicator based on the difference between the first and second ETC values. The ETL indicator provides feedback regarding a degree of energy transfer associated with at least one of the first and second positions.

Optionally, the at least one processor may be configured to change the ETL indicator from a first ETL indicator associated with the first ETC value to a second ETL indicator associated with the second ETC value. The change may indicate a change in the degree of energy transfer when moving the external antenna from the first position to the second position. The at least one processor may be configured to indicate whether the change in the degree of energy transfer represents an increase or a decrease in the degree of energy transfer. The degree of energy transfer may increase when the analyzing determines that the first ETC value may be greater than the second ETC value. The degree of energy transfer may decrease when the analyzing determines that the first ETC value may be less than the second ETC value.

Optionally, the first and second positions may correspond to current and previous positions, respectively, of the external antenna with respect to the implanted antenna. The at least one processor may be configured to change the ETL indicator to indicate a decrease in the degree of energy transfer when the current position is associated with a first ETC value that may be lower than the second ETC value associated with the previous position and the at least one processor may be configured to change the ETL indicator to indicate an increase in the degree of energy transfer when the current position is associated with a first ETC value that may be greater than the second ETC value associated with the previous position. The at least one processor may be configured to obtain movement data indicative of movement of the external antenna relative to a reference, the providing including changing the ETL indicator based on the movement data.

Optionally, the at least one processor may be configured to analyze the first and second ETC values in combination with the movement data to determine whether a change between the first and second ETC values was accompanied by movement of the external antenna. The at least one processor may be configured to estimate a current level of available power of the PIMD based on at least a predetermined value of power consumption of the PIMD for at least one PIMD operation and a change in the first ETC value over the second ETC value over a select time interval. The at least one processor may be configured to account for power calculation noise originating from moving the external antenna from the first position to the second position. The at least one processor may be configured to transmit instructions to the PIMD to initiate a select PIMD operation if the current level of available power of the PIMD is above a threshold value for the select PIMD operation. The at least one processor may be configured to delay a select PIMD operation if the current level of available power of the PIMD is below a threshold value for the select PIMD operation.

In accordance with embodiments herein, a computer implemented method is provided. The method receives an energizing signal at an implanted antenna of a passive implanted medical device (PIMD). the energizing signal is transmitted from an external antenna, while the external antenna is at first and second positions. The method is under control of one or more processors of the PIMD configured with program instructions. The method obtains first and second energy transfer characteristic (ETC) values and transmits, at the implanted antenna, the first and second ETC values associated with the first and second positions, respectively.

Optionally, the method may comprise estimating a current level of available power of the PIMD based on at least a predetermined value of power consumption of the PIMD for at least one PIMD operation and a change in the first and second ETC values over a select time interval. The method may comprise mathematically combining a select number of ETC values to determine, respectively, the first and second ETC values.

In accordance with embodiments herein, a passive implantable medical device (PIMD) is provided. The PIMD includes an implanted antenna configured to receive an energizing signal from an external antenna, coupled to a local external device (LED). The energizing signal is transmitted while the external antenna is at first and second position. The PIMD includes at least one PIMD processor and a PIMD memory coupled to the at least one PIMD processor. The memory stores program instructions. The program instructions are executable by the at least one PIMD processor to obtain first and second energy transfer characteristic (ETC) values and transmit, at the implanted antenna, first and second ETC values associated with the first and second positions, respectively.

Optionally, the at least one processor may be configured to estimate a current level of available power of the PIMD based on at least a predetermined value of power consumption of the PIMD for at least one PIMD operation and a change in the first and second ETC values over a select time interval. The at least one processor may be configured to mathematically combine a select number of ETC values to determine, respectively, the first and second ETC values.

DETAILED DESCRIPTION

Figure 1:
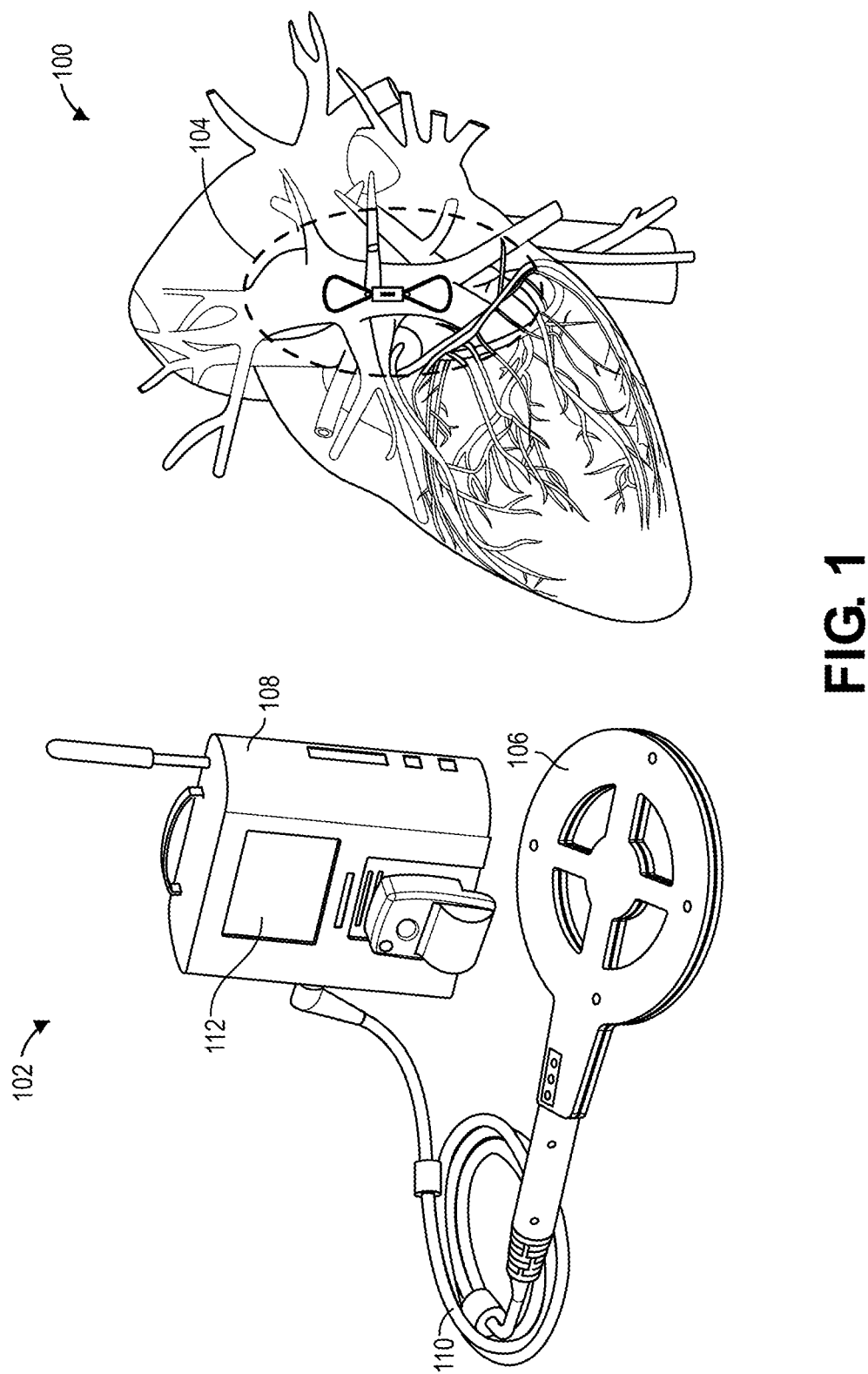
FIG. 1 illustrates an example of a system comprising a passive implantable medical device (PIMD) located in a pulmonary artery and a local external device in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Terms

As used herein, the term "passive", when used to describe an implantable medical device (e.g., a sensor), shall mean that the circuitry of the implantable medical device (IMD) is configured to receive power through a wireless interface. The passive IMD may be configured to receive power through the wireless interface continuously or intermittently from an external source during operation and does not include a standalone power source capable of powering all or substantially all of the circuitry of the IMD at an operational level for an extended period of time. Additionally or alternatively, the passive IMD may be configured to receive power through a wireless interface intermittently from an external source during a charging operation, and does include a standalone power source capable of powering all or substantially all of the circuitry of the IMD at an operational level for an extended period of time. By way of example, a passive implantable medical device (PIMD) comprises circuit components (e.g., capacitors, resistors, inductors, and the like) and a power source that is capable of supplying power to implement a secondary PIMD operation (e.g., monitoring the degree of energy transfer to the PIMD) but incapable of supplying a threshold level of power required to implement a primary PIMD operation (e.g., monitoring a physiological parameter of interest and/or transmitting data) without receiving additional power from an external source.

The terms "degree of energy transfer" and "DET" shall mean a rate at which energy is received by a circuit that is configured to temporarily store or use the energy as power, and/or shall also mean an amount of energy that is currently retained by the circuit.

The term "energy transfer characteristic" or "ETC" shall mean any electrical characteristic, whether directly measured, or calculated or estimated based on at least one measured circuit characteristic, where the electrical characteristic varies depending on the degree of energy transfer experienced by the circuit. The ETC may include voltage, current, resistance, power, frequency, and the like.

The terms "energy transfer level indicator", "ETL indicator", "energy level indicator", and "EL indicator" shall mean an indicator of the degree of energy transfer that may be perceived (e.g., heard, seen, felt) by a user. The indicator shall provide feedback to a user to guide positioning of the external antenna relative to the implanted antenna to manage (e.g., improve or optimize) at least one of the degrees of energy transfer to a PIMD, the strength of a response signal from a PIMD, or the level of available power of the PIMD. For example, the indicator may comprise one or more of an audible indicator that varies in volume, pitch, and/or frequency or that provides verbal cues, a haptic indicator that varies in strength and/or frequency, and a visual indicator that changes color, shape, and/or size, and/or flashes (e.g., an element displayed on a user interface of the local external device that changes from red to yellow to green and/or that varies in height), where the variation is proportional to, and indicative of, the degree of energy transfer.

The term "obtain" or "obtaining", as used in connection with data, signals, information and the like, includes at least one of i) accessing memory of a local external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of a PIMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from a PIMD and/or a remote server. The obtaining operation may be from the perspective of a remote server, such as when receiving the data, signals, information, etc. at a network interface from a local external device and/or directly from a PIMD. The remote server may also obtain the data, signals, information, etc. from local memory and/or from other memory, such as within a cloud storage environment and/or from the memory of a workstation or clinician external programmer.

Overview

In accordance with embodiments herein, methods and systems are provided for guiding positioning of an external antenna coupled to a local device relative to an implanted antenna of a passive implanted (or implantable) medical device (PIMD) in order to manage the degree of energy transfer between the external antenna and the implanted antenna. For example, managing the degree of energy transfer between the external antenna and the implanted antenna may include ensuring a sufficient degree of energy transfer to power primary PIMD operations and, optionally, secondary PIMD operations. Embodiments herein avoid certain difficulties in implementing PIMDs requiring wireless power from external local devices for operation such as difficulty in aligning the external antenna with the implanted antenna, whose exact location and orientation cannot be seen by a user, and insufficient power delivery to the implanted antenna to ensure stable operation of the passive implanted medical device.

Embodiments herein monitor an energy transfer characteristic of the PIMD and, based thereon, provide feedback to a user to indicate whether recent changes in position of the external antenna relative to the internal antenna increased or decreased the degree of energy transfer. The feedback, provided as an ETL indicator or EL indicator, may guide a user to move the external antenna relative to the implanted antenna of the PIMD in order to increase the degree of energy transfer to the PIMD, improve response signal strength from the PIMD, and/or ensure a sufficient level of available power to initiate a select operation of the PIMD.

Passive Implantable Medical Device Background

Embodiments may be implemented in connection with one or more PIMDs. Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", U.S. Pat. No. 9,653,926 entitled "Physical Property Sensor with Active Electronic Circuit and Wireless Power and Data Transmission", and U.S. Pat. No. 9,792,469 entitled "Wireless Physical Property Sensor with Digital Communications" which are all hereby incorporated by reference in their respective entireties.

In one example, the PIMD may be configured to convert a sensed physiological parameter into an electrical signal. For example, the PIMD may convert (or transduce) sensed temperature changes to changes in resistance (e.g., a temperature-sensitive resistor), convert sensed changes in pressure to changes in capacitance (e.g., a pressure-sensitive capacitor), convert sensed stress changes to changes in resistance via (e.g., a stress sensitive resistor), and the like. When interrogated by a local external device, PIMDs may, in a primary operation, provide data indicative of diagnostic health data for further processing, transmission, display, storage, and the like to the local external device. The example of a passive wireless sensor (as the PIMD) configured to monitor pressure in a primary PIMD operation is used in the following description solely for the sake of clarity and is not intended to limit the disclosure in any way.

Local External Device Background

FIG. 1 illustrates an exemplary system 100 comprising a local external device 102 and a passive implanted (or implantable) medical device (PIMD) 104. The local external device 102 comprises an external antenna (or coupling loop, magnetic loop, loop) 106 operably coupled to a base unit 108 via a cable 110. The base unit 108 includes a user interface. The user interface may, for example and without limitation, include a touch sensitive display 112 for inputting information and/or data, operating the base unit 108, and displaying information and/or data to a user. The local external device 102 may include one or more structural and/or functional aspects of the device(s) described in U.S. Pat. No. 7,245,117 entitled "Communicating with Implanted Wireless Sensor", U.S. Pat. No. 7,492,144 entitled "Preventing False Locks in a System that Communicates with an Implanted Wireless Sensor", U.S. Pat. No. 7,432,723 entitled "Coupling Loop", U.S. Pat. No. 7,432,723 entitled "Communication System with Antenna Box Amplifier", U.S. Pat. No. 8,111,150 entitled "Physiological Data Acquisition and Management System for Use with an Implanted Wireless Sensor", and U.S. Pat. No. 7,667,547 entitled "Loosely-coupled Oscillator", which are all hereby incorporated by reference in their respective entireties.

The local external device 102 is used to interrogate the PIMD 104 to monitor a physiological parameter of interest. For example, the local external device 102 determines the resonant frequency of the PIMD 104, where the resonant frequency varies in response to a measured physiological parameter of interest such as, for example and without limitation, pressure. Interrogation includes energizing the PIMD 104 and receiving at least one type of return signal from the PIMD 104. The local external device 102 may energize the PIMD 104 with a burst of RF energy. The energizing signal may be a low duty cycle, gated burst of RF energy of a predetermined frequency or set of frequencies at predetermined amplitude. For example, the duty cycle of the energizing signal may range from 0.1% to 50%. In one example, the local external device 102 energizes the PIMD 104 with a 30-37 MHz fundamental signal at a pulse repetition rate of 100 kHz with a duty cycle of 20%. The energizing signal is coupled to the PIMD 104 via inductive coupling between an internal antenna of the PIMD 104 and the external antenna 106. The energizing signal induces a current in the PIMD 104 which has a maximum amplitude at the resonant frequency of the PIMD 104. When the energizing signal induces a current in the PIMD 104, the PIMD 104 charges exponentially to a steady-state amplitude that is proportional to the coupling efficiency (or DET) between the implanted antenna of the PIMD 104 and external antenna 106, distance between the implanted antenna and external antenna 106, and the RF power.

Figure 2:
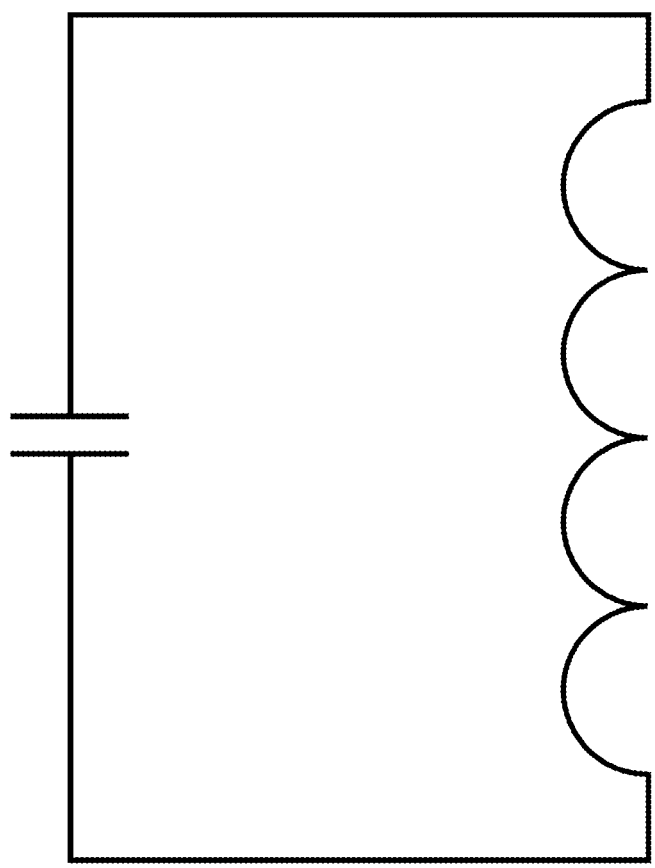
FIG. 2 illustrates an example of PMID 104 based on Inductor-capacitor (LC) resonant circuit.

FIG. 2 shows an example of PIMD 104 based on an inductive-capacitive (LC) resonant circuit in accordance with embodiments herein.

Figure 3A:
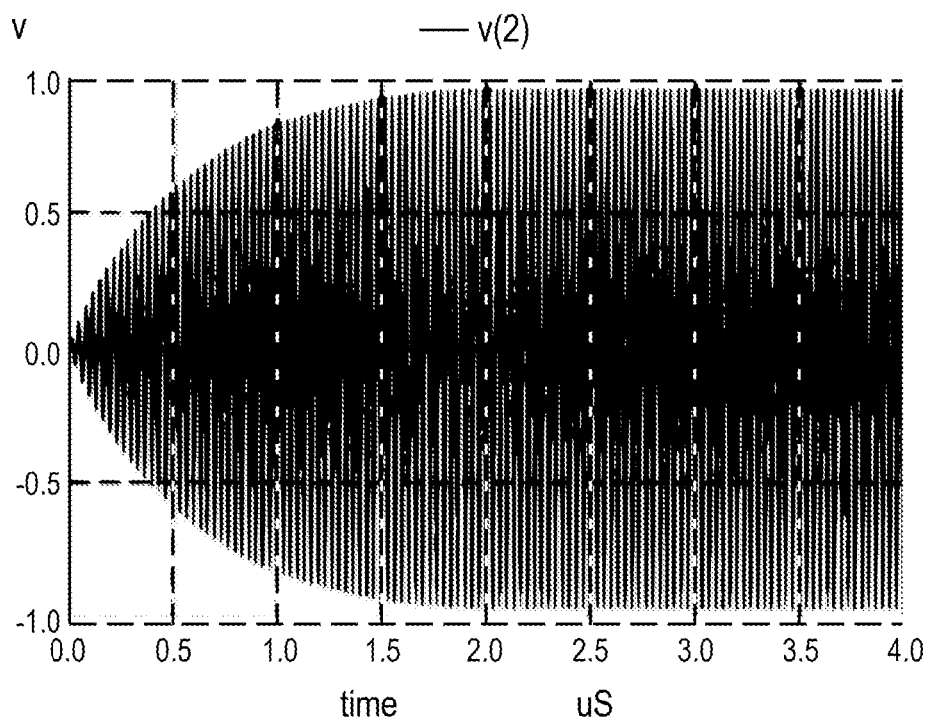
FIG. 3A is a graph illustrating an exemplary charging response of a resonant circuit in accordance with an embodiment of the invention.

FIG. 3A shows the charging response of a typical resonant circuit (e.g., LC circuit) to a burst of RF energy at the resonant frequency of the circuit. The speed at which the PIMD 104 charges is directly related to a Q (quality factor) of the PIMD. Therefore, an "on time" of the pulse repetition duty cycle is managed for the Q of the PIMD. The local external device 102 receives a ring down response of the PIMD 104 via inductive (or magnetic) coupling and, based thereon, determines the resonant frequency of the PIMD.

Figure 3B:
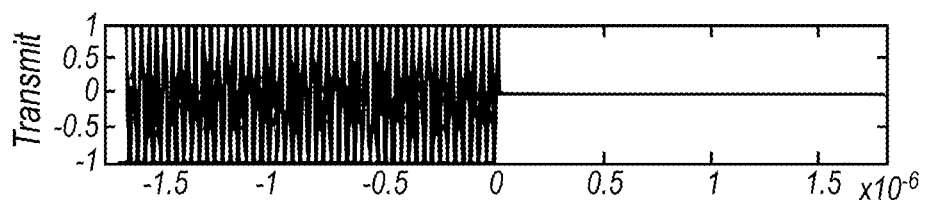
FIG. 3B is a graph illustrating an exemplary energizing signal in accordance with an embodiment of the invention.
Figure 3C:
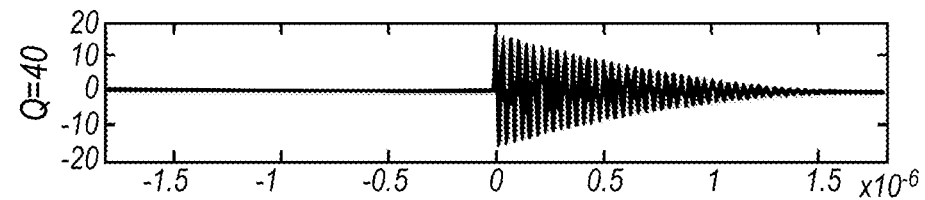
FIG. 3C is a graph illustrating an exemplary coupled signal in accordance with an embodiment of the invention.

FIG. 3B illustrates an example energizing signal and FIG. 3C illustrates an example coupled signal for a select value of Q (quality factor) for the PIMD 104. When the local external device 102 is coupled at or near the resonant frequency of the PIMD 104, an amplitude of a PIMD return signal is maximized, and a phase of the PIMD return signal will be close to zero degrees with respect to a phase of the energizing signal. The PIMD return signal (e.g., the ring down response) is processed via phase-locked-loops to steer the frequency and phase of a next energizing pulse of the local external device 102.

Figure 4A:
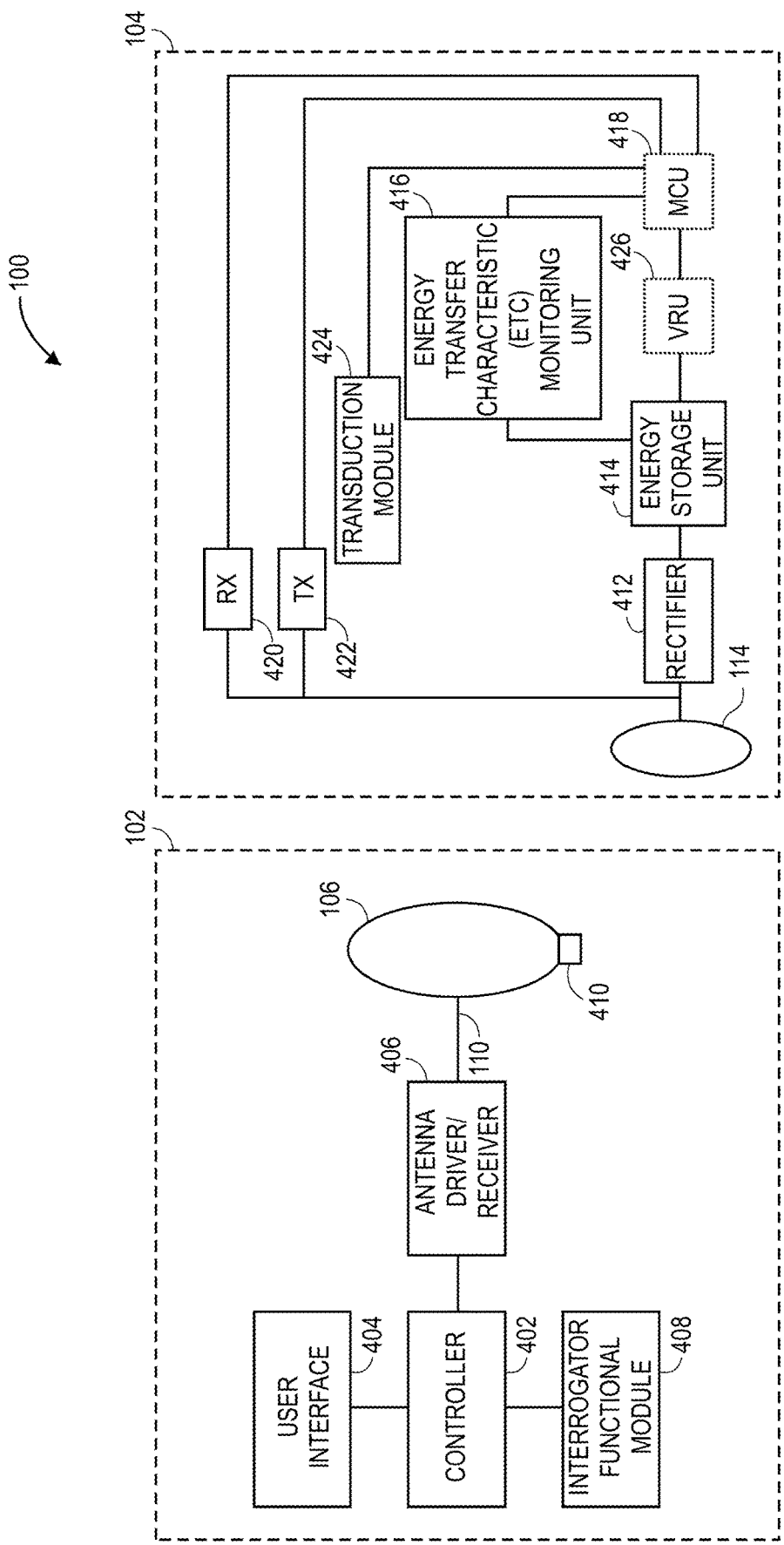
FIG. 4A illustrates a simple block diagram of at least a portion of the circuitry of the local external device and an example PIMD in accordance with embodiments herein.

In an additional or alternative embodiment, the system 100 may, during a first energizing periods, accumulate and store energy received wirelessly via the internal antenna 114 from the external antenna 106 of the local external device 102 using the energy storage unit (e.g., a capacitor or rechargeable battery) of the PIMD 104 (see FIG. 4A). The first energizing periods may be a gated burst of RF energy of a predetermined frequency or set of frequencies at predetermined amplitude with a constant or a varying duty cycle. For example, the duty cycle of the energizing signal may range from 50% to 95%. In one example, the local external device 102 energizes the PIMD 104 with an industrial, scientific, and medical (ISM) radio band frequency signal at a pulse repetition rate of 5 Hz to 500 Hz. The system 100, during second periods of time in which energy is not received from the local external device 102, may use the circuitry of the PIMD 104, which is powered by the energy stored on the energy storage unit (e.g., a capacitor or rechargeable battery), to perform at least one of a plurality of predetermined operations of the PIMD 104. In accordance with an embodiment, the plurality of predetermined operations includes the primary and/or the secondary PIMD operations. The second periods of time may or may not be interleaved with the first energizing periods. Additionally or alternatively, the local external device 102 wireless energizes the PIMD 104 continuously and the PIMD 104 performs the primary and/or the secondary operations at the predetermined intervals.

System for Managing Energy Transfer

FIG. 4A illustrates a simple block diagram of at least a portion of the circuitry within a local external device 102 and a PIMD 104 of the system 100 of FIG. 1 utilized in accordance with embodiments herein.

The local external device 102 includes a controller 402 that is operably coupled to a user interface 404 and to an external antenna 106 via an antenna driver/receiver 406 and a cable 110. The external antenna 106 includes an energizing loop (e.g., a coil) and a receiving loop (e.g., a coil). The energizing loop may be positioned concentrically with the receiving loop or positioned non-concentrically to reduce interference to each other. Optionally the external antenna 106 may include one antenna loop used for both energizing and receiving functions. The controller 402 also utilizes or communicates with various other electronic components, firmware, software, and the like that generally perform PIMD interrogation and signal processing functions (as generally denoted by interrogator functional module 408) as described further below.

The PIMD 104 includes an implanted antenna 114, a rectifier 412, an energy storage unit 414, an ETC monitoring unit 416, a microcontroller unit (MCU) 418, a receiver 420, a transmitter 422, and a transduction module 424. The energy storage unit 414 may be an energy storage capacitor, a battery, a rechargeable battery or the like. In operation, AC energy received by the implanted antenna 114 during interrogation by the local external device 102 is rectified at rectifier 412 to apply a voltage across and charge the energy storage unit 414. Optionally, a voltage regulation unit (VRU) 426 may be placed in between the energy storage unit 414 and the MCU 418 to control the supply voltage for the MCU 418 and the transduction module 424. As the energy storage unit 414 charges and PIMD 104 initiates operation, the MCU 418 obtains current ETC values from the ETC monitoring unit 416 (e.g., the voltage applied across the energy storage unit 414). The MCU 418 also receives and processes signals and/or data transmitted by the local external device 102 to the receiver 420. Optionally, the MCU 418 may also obtain values indicative of a physiological parameter of interest from the transduction module 424. The MCU 418 transmits signals indicative of current ETC values and, optionally, current values of the physiological parameter of interest, to the local external device 102 through the transmitter 422 and implanted antenna 114 on a continuous or select basis.

In an alternative embodiment, the PIMD 104 may include a dedicated receive antenna tuned to a first frequency and a dedicated transmit antenna tuned to a second frequency different from the first frequency to enable simultaneous transmission and receipt of energy, data, and/or command signals with the local external device 102. The transduction module 424 may be implemented as a digital and/or an analog circuit and may be configured to measure any of a number of physiological parameters of interest.

Figure 4B:
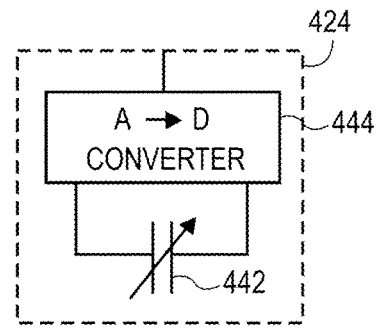
FIG. 4B illustrates an example of a digital transduction module for implementation in the PIMD of FIG. 4A in accordance with embodiments herein.

FIG. 4B illustrates one implementation of a digital transduction module 424. For example, the digital transduction module 424 may include a pressure-sensitive capacitor 442 operably coupled to a digital to analog converter 444 that directly converts capacitance values to a digital number. The pressure-sensitive capacitor 442 varies capacitance in response to changes in local pressure. Upon the system 100 initiating a primary PIMD operation, the digital to analog converter 444 obtains analog capacitance values on a continuous or select basis, converts the analog capacitance values to digital values, and facilitates transmission of the digital values indicative of capacitance to the local external device 102.

The ETC monitoring unit 416 monitors ETC values of the energy storage unit 414 that indicate the degree of energy transfer between the implanted antenna 114 and the external antenna 106. In one example, where the implanted antenna 114 and the external antenna 106 each comprise a loop antenna, the degree of energy transfer between the implanted antenna 114 and the external antenna 106 will achieve a select level (e.g., maximized) when the implanted antenna 114 and external antenna 106 are arranged, with respect to one another, concentric, parallel, and/or spaced apart by a shortest distance. For example, the degree of energy transfer between the implanted antenna 114 and the external antenna 106 will be increased when a magnetic flux lines of the external antenna 106 is aligned with a magnetic flux lines of the implanted antenna 114. In many cases, while there is some degree of predictability in PIMD 104 location and orientation, final PIMD location and orientation (and, thus, final implanted antenna 114 location and orientation) is not necessarily known to the user. Furthermore, a user of the local external device 102 will be unable to see the exact location and orientation of the PIMD 104 and thus cannot visually align the implanted antenna 114 and the external antenna 106.

In order to ameliorate issues in implementing wireless systems, the ETC monitoring unit 416 monitors ETC values of the energy storage unit 414 that indicate the degree of energy transfer between the external antenna 106 and implanted antenna 114. The ETC values may be monitored and used to provide feedback to a user via an ETL indicator to indicate whether recent changes in position of the external antenna 106 relative to the internal antenna 114 increased or decreased the degree of energy transfer as further described below.

The MCU 418 obtains ETC values from the ETC monitoring unit 416 and transmits signals indicative of ETC values to the local external device 102. Additionally or alternatively, the MCU 418 may be configured to obtain and mathematically combine an ensemble of ETC values, such as by detecting peaks in or determining the average, mean, median, etc., of the values over a select time to obtain composite ETC values. Exemplary ETC values (or composite ETC values) may range from 1.2V to 5V, from 10 µA to 500 µA, and from 10 µW to 2500 µW, based on the relative position of the implanted antenna 114 and the external antenna 106.

The MCU 418 transmits signals indicative of ETC values (or composite ETC values) to the local external device 102 through the transmitter 422 and implanted antenna 114 on a continuous or select basis. The MCU 418 may transmit the ETC values to the local external device 102 using digital modulation techniques such as amplitude shift keying (ASK), phase shift keying (PSK), frequency shift keying (FSK), on-off keying (OOK) and the like.

In one example, the MCU 418 transmits ETC values (or composite ETC values) to the local external device 102 as part of an initial setup process. The external antenna 106 may be placed in sufficient proximity to the internal antenna 114 to initiate PIMD operation. Upon receiving power, the system 100 may be configured such that the local external device 102 and the PIMD 104 initiate an energy transfer (or power) management sequence prior to initiating any primary PIMD operations (e.g., measuring the physiological parameter of interest). The energy transfer management sequence provides feedback to guide a user in managing the degree of energy transfer between the external antenna 106 and the implanted antenna 114.

In additional or alternative examples, the MCU 418 transmits ETC values (or composite ETC values) to the local external device 102 on a continuous or periodic basis (e.g., 10×/sec, 1×/5 sec). The system 100 may continuously or periodically confirm or re-confirm that the relative position of the external antenna 106 and implanted antenna 114 is providing a degree of energy transfer sufficient to ensure stable operation of the PIMD 104, or provide feedback to guide a user to reposition the external antenna 106 relative to the implanted antenna 114 to increase the degree of energy transfer to the PIMD 104.

The controller 402 of local external device 102 receives and processes the ETC values (or composite ETC values) in order to provide feedback to guide a user. For example, ETC values (or composite ETC values) ranging from 1.2V to 5V, from 10 µA to 500 µA, from 10 µW to 2500 µW, and the like may be correlated to a range of values of an ETL indicator or ET indicator implemented on the local external device 102. The feedback provided by the ETL indicator may guide a user to move the external antenna 106 relative to the implanted antenna 114 in order to manage the degree of energy transfer therebetween (e.g., increase the degree of energy transfer).

Optionally, a movement detection module 410 may be operably coupled to the external antenna 106 and configured to provide movement data to the controller 402 of the local external device 102. In one example, the movement detection module 410 may comprise at least one accelerometer. The controller 402 may obtain movement data and correlate whether or not changes in the ETC value correspond to changes in position of the external antenna 106. When the movement data indicates that no position change occurs, the change in ETC values may be due to either charging or discharging of the energy storage unit 414. In another example, the movement detection module 410 may comprise up to three accelerometers and/or up to three gyroscopes, and, optionally, reference points on the external antenna 106. The controller 402 may obtain movement data and determine if changes in ETC values are due to translation and/or rotation of the external antenna 106 relative to a reference (e.g., gravity) using up to all six degrees of freedom. Here, the ETL indicator of the local external device 102 may provide more detailed feedback to a user, guiding a user to translate and/or rotate the external antenna 106 with respect to one or more axis to manage the degree of energy transfer between the external antenna 106 and the internal antenna 114.

Figure 5:
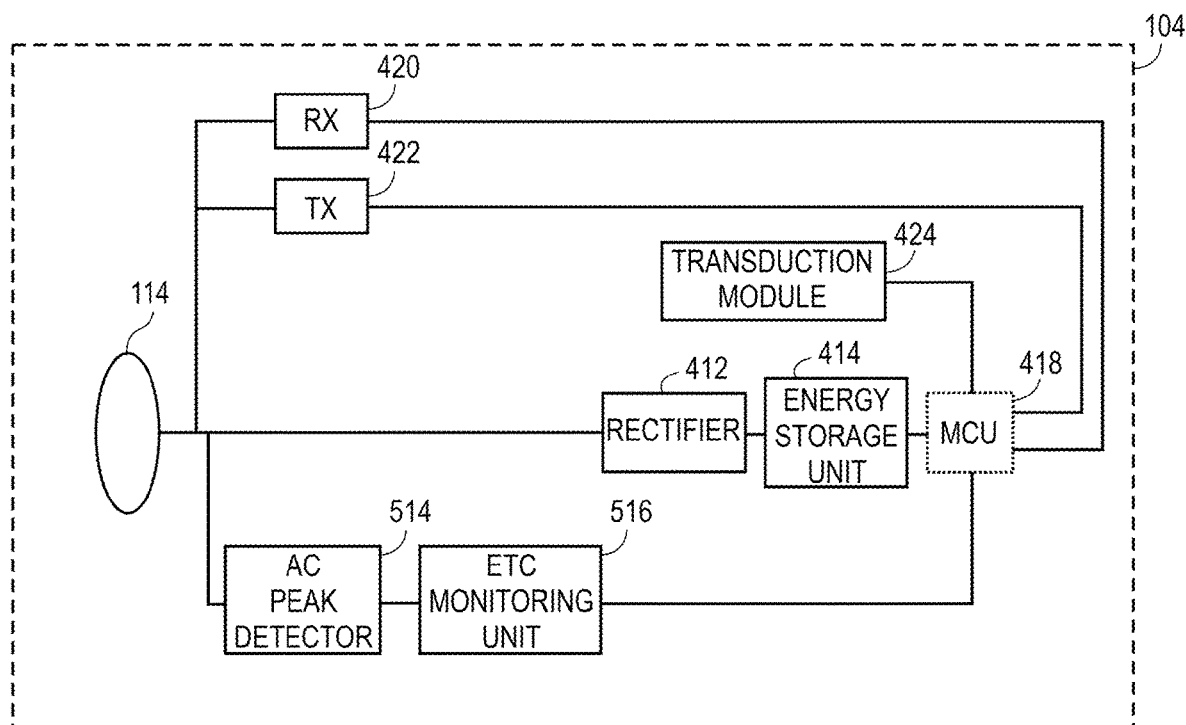
FIG. 5 illustrates a simple block diagram of at least a portion of the circuitry of an example PIMD in accordance with embodiments herein.

FIG. 5 illustrates another example of a PIMD 104 that is substantially identical to the PIMD of FIG. 4 except for the following differences. An AC peak detection unit 5514 is implemented between the implanted antenna 114 and the ETC monitoring unit 516. The AC peak detection unit 514 may include dedicated rectifiers and capacitors (C), and, optionally, a discharge resistor (R). The capacitor value of the AC peak detection unit 514 is sufficiently small that a discharge time (or RC time constant) is at least one order of magnitude faster than the voltage change time of energy storage unit 414, resulting in i) ETC values that are smaller than those measurable across the energy storage unit 414 and ii) ETC values corresponding to the relatively fast changing AC side of the implanted antenna 114. The ETC monitoring unit 516 is operably coupled to the MCU 418 and operates in the same manner as ETC monitoring unit 416 except that ETC monitoring unit 516 may enable feedback based on ETC values prior to charging of the energy storage unit 414.

Method for Manacling Energy Transfer

Figure 6:
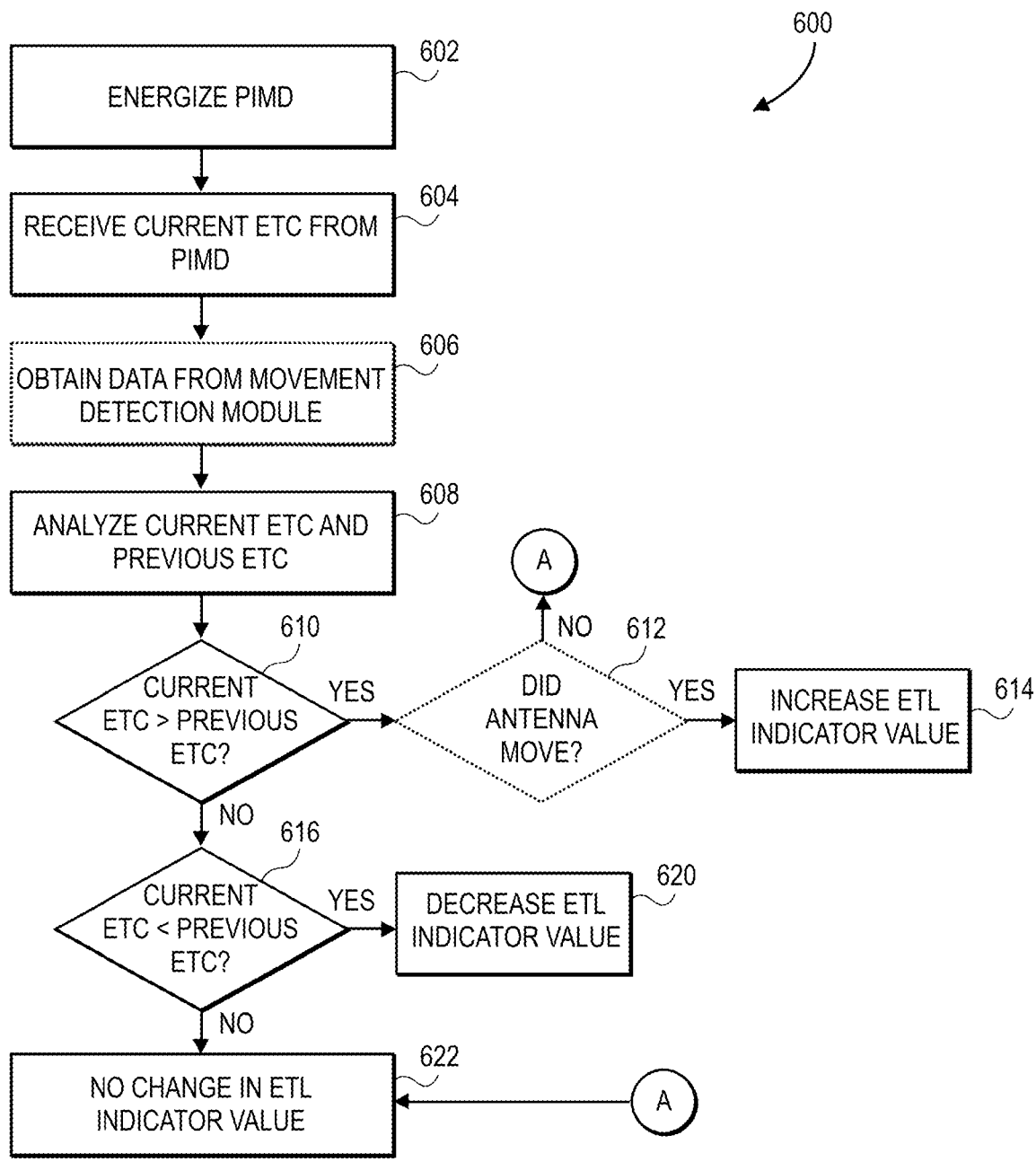
FIG. 6 illustrates an exemplary method for guiding a user to manage the degree of energy transfer between an external antenna and an implanted antenna in accordance with embodiments herein.

FIG. 6 illustrates a computer-implemented method 600 for guiding positioning of an external antenna 106 relative to a reference in order to manage the degree of energy transfer between the external antenna 106 and the implanted antenna 114. Managing the degree of energy transfer may include achieving a desired degree of energy transfer between the external antenna 106 and the implanted antenna 114 in accordance with embodiments herein. It should be recognized that while the operations of method 600 are described in a somewhat serial manner, one or more of the operations of method 600 may be continuous and/or performed in parallel with one another. For example, the various operations of the local external device 102 may be continuous and performed in parallel with the operations performed by the PIMD 104. Also, unless otherwise indicated, each operation of method 600 is performed under the control of one or more processors configured with program instructions.

Beginning at 602, the one or more processors of the local external device 102 direct the antenna driver 406 to transmit an energizing signal. The energizing signal is transmitted while the external antenna 106 is at first and second positions. The first and second positions may be different, the same, or substantially the same. The energizing signal is coupled to the PIMD 104 through coupling (e.g., inductive coupling) between the external antenna 106 and the implanted antenna 114. The coupled energizing signal induces a current in the PIMD 104 that charges an energy storage unit 414 of the PIMD 104, causing the PIMD 104 to initiate operation. As the PIMD 104 initiates operation, the one or more processors of the PIMD 104 obtain a current ETC value from the ETC monitoring unit 416. Optionally, the one or more processors of the PIMD 104 may obtain an ensemble of current ETC values and mathematically combine the ensemble of current ETC values, such as through averaging, obtaining a mean, median, etc., to form a composite current ETC value (e.g., a moving average). The one or more processors of the PIMD 104 transmit the current ETC value (or composite current ETC value) to the local external device 102.

At 604, the local external device 102 receives a communication from the PIMD 104 indicating the current ETC value (or composite current ETC value) as part of the communication protocol utilized. For example, the communication is performed by MCU 418 directing Tx 422 to send data through implanted antenna 114 using digital modulation techniques such as amplitude shift keying (ASK), phase shift keying (PSK), frequency shift keying (FSK), on-off keying (OOK) and the like.

Optionally, at 606, the one or more processors of the local external device 102 obtain movement data from the movement detection module 410 that is physically connected to the external antenna 106. The movement data indicates the local movement of the external antenna 106 with respect to a reference (e.g., an antenna has been moved up down, left, right, forward, backward, or has been rotated about one or more axis relative to gravity).

The operations at 602, 604, and 606 may be performed at various times before, after, or in combination with, interrogation of the PIMD 104 by the local external device 102 to monitor a physiological parameter of interest (e.g., pressure).

At 608, the one or more processors of the local external device 102 analyze the current ETC value and previous ETC value(s). Optionally, the one or more processors may obtain an ensemble of previous ETC values and mathematically combine the ensemble of previous ETC values, such as through averaging, obtaining a mean, median, etc., to form a composite previous ETC value (e.g., a moving average).

At 610, the one or more processors of the local external device 102 compare the current ETC value to the previous ETC value (or composite previous ETC value) to determine if the current ETC value is greater than the previous ETC value. If the current ETC value is greater than the previous ETC value, the process interprets the condition to represent an increase in the degree of energy transfer between the current and previous measurements, and thus flow moves to 614. At 614, the one or more processors of the local external device 102 increase a value of an ETL indicator. An increase in the ETL indicator informs the user that a current position of the external antenna 106 increased the degree of energy transfer as compared to a prior position of the external antenna 106 and the movement was favorable.

Returning to 610, if the current ETC value is not greater than the previous ETC value, the process interprets the condition to not represent an increase in the degree of energy transfer, and flow moves to 616.

Optionally, a movement determination may be added at 612. If the current ETC value is greater than the previous ETC value, flow may move from 610 to 612. At 612, the one or more processors of the local external device 102 analyze movement data to determine if the external antenna 106 changed position (e.g., was translated or rotated) between measurement of the current ETC value and the previous ETC value. The first position of the external antenna 106 may be different, the same, or substantially the same as the second position of the external antenna 106. If the one or more processors determine at 612 that no movement occurred and the current ETC value is greater than the previous ETC value, the process interprets the condition to represent no change in the degree of energy transfer and flow moves from 612 to 622. At 622, the one or more processors do not increase or decrease the value of the ETL indicator, but instead maintain the value of the ETL indicator. Maintaining a constant ETL indicator informs the user that the status quo is maintained. For example, an increase in the current ETC value over the previous ETC value may occur at the onset of interrogation, as the energy storage unit 414 of the PIMD 104 charges but while the user holds the external antenna 106 in a single position.

Returning to 612, if movement occurred and the current ETC value is greater than the previous ETC value, the process interprets the condition to represent an increase in the degree of energy transfer, and thus flow moves to 614. At 614, the one or more processors of the local external device 102 increase the value of the ETL indicator. An increase in the ETL indicator informs the user that the position of the external antenna 106 relative to the implanted antenna 114 corresponding to the current ETC value increased the degree of energy transfer over the position of the external antenna 106 relative to the implanted antenna 114 corresponding to the previous ETC value and the movement was favorable.

At 616, the one or more processors of the local external device 102 compare the current ETC value to the previous ETC value to determine if the current ETC value is less than the previous ETC value. If the current ETC value is less than the previous ETC value, the process interprets the condition to represent a decrease in the degree of energy transfer, and thus flow moves to 620. At 620, the one or more processors decrease the value of the ETL indicator. A decrease in the ETL indicator informs the user that the current position of the external antenna 106 relative to the implanted antenna 114 caused a decrease in the degree of energy transfer as compared to a degree of energy transfer associated with the previous position of the external antenna 106 relative to the implanted antenna 114 and that the movement was not favorable.

Returning to 616, if the current ETC value is not less than or greater than the previous ETC value, the process interprets the condition to not represent a decrease or an increase in the degree of energy transfer, and thus flow moves to 622. At 622, the one or more processors do not increase or decrease the value of the ETL indicator, but instead maintain the value of the ETL indicator. Maintaining a constant ETL indicator informs the user that the status quo is maintained.

Method for Managing Available Power

Figure 7:
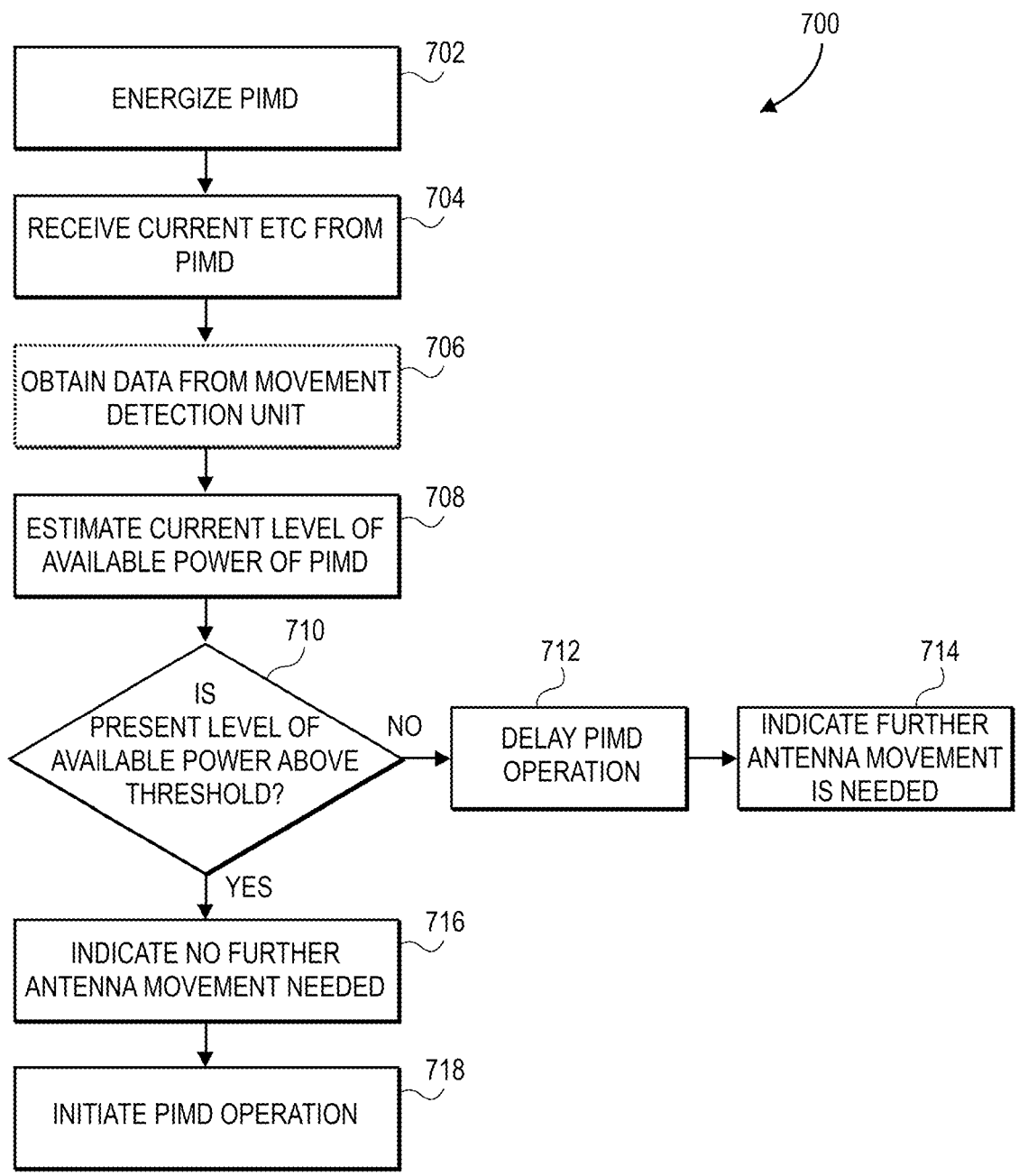
FIG. 7 illustrates an exemplary method for monitoring the current level of available power of a PIMD in accordance with embodiments herein.

FIG. 7 illustrates a computer-implemented method 700 for guiding positioning of an external antenna 106 relative to an implanted antenna 114 in order to manage the available power of a PIMD in accordance with embodiments herein. Managing the available power of a PIMD may include achieving a desired degree of available power of the PIMD 104 and/or achieving a desired degree of energy transfer between the external antenna 106 and the implanted antenna 114. Method 700 may be implemented as an alternative to or in addition to method 600. It should be recognized that while the operations of method 700 are described in a somewhat serial manner, one or more of the operations of method 700 may be continuous and/or performed in parallel with one another and/or with the operations of method 600. For example, the various operations of the local external device 102 may be continuous and performed in parallel with the operations performed by the PIMD 104. Also, unless otherwise indicated, each operation of method 700 is performed under the control of one or more processors configured with program instructions.

Beginning at 702, similar to operation 602 of method 600, the one or more processors of the local external device 102 direct the antenna driver 406 to transmit an energizing signal and the energizing signal is coupled to the PIMD 104 through coupling (e.g., inductive coupling) between the external antenna 106 and the implanted antenna 114. The energizing signal is transmitted while the external antenna 106 is at first and second positions. The first and second positions may be different, the same, or substantially the same. The coupled energizing signal induces a current in the PIMD 104 that charges an energy storage unit 414 of the PIMD 104, causing the PIMD 104 to initiate operation. As the PIMD 104 initiates operation, the one or more processors of the PIMD 104 obtain a current ETC value from the ETC monitoring unit 416 and transmit the current ETC value to the local external device 102. Optionally, the one or more processors of the PIMD 104 may obtain an ensemble of current ETC values and mathematically combine the ensemble of current ETC values, such as through averaging, obtaining a mean, median, etc., to form a composite current ETC value (e.g., a moving average). Then, the one or more processors transmit the current ETC value (or composite current ETC value) to the local external device 102.

At 704, similar to operation 604 of method 600, the local external device 102 receives a communication from the PIMD 104 indicating the current ETC value.

Optionally, at 706, similar to operation 606 of method 600, the one or more processors of the local external device 102 obtain movement data from the movement detection module 410 operably coupled to the external antenna 106. The movement data indicates the local movement of the external antenna 106 with respect to a reference (e.g., an antenna has been moved up down, left, right, forward, backward, or has been rotated about one or more axis).

The operations at 702, 704, and 706 may be performed at various times before, after, or in combination with, interrogation of the PIMD 104 by the local external device 102 to monitor a physiological parameter of interest (e.g., pressure).

At 708, the one or more processors of the local external device 102 analyze the current ETC value and previous ETC value to estimate or determine a current level of available power of the PIMD 104. The current level of available power may be estimated or determined by calculating a change in ETC values over a select time interval and accounting for the predetermined power consumption of the PIMD 104 during one or more select PIMD operations occurring during the select time interval. The change in ETC values over a select time interval may be a change between the current ETC value and at least one previous ETC value, a change between multiple current ETC values sampled over a select time interval, or the like. Optionally, the estimation or determination of the current level of available power may also include accounting for a value of power calculation noise. Power calculation noise may originate from a change in relative position (e.g., translation or rotation) between the external antenna 106 and the implanted antenna 114 over the select time interval. Values of power calculation noise may be estimated or determined based, at least in part, on movement data obtained from the movement detection module 410.

At 710, the one or more processors of the local external device 102 determine whether the current level of available power meets or exceeds a threshold level of power required to initiate a select PIMD operation. For example, the select PIMD operation may be a primary PIMD operation.

If the current level of available power of the PIMD 104 does not exceed the threshold level of power required for the select PIMD operation, the process interprets the condition to represent insufficient available power for the select PIMD operation, and thus flow moves to 712. At 712, the one or more processors delay execution of the select PIMD operation and flow moves to 714. At 714, the one or more processors set a low value of an EL indicator or an ETL indicator, informing the user that the current level of available power of the PIMD 104 is insufficient to initiate the select PIMD operation and that further movement of the external antenna 106 is needed.

Returning to 710, if the current level of available power of the PIMD 104 meets or exceeds the threshold level of power required for the select PIMD operation, the process interprets the condition to represent sufficient available power for the select PIMD operation, and thus flow moves to 716. At 716, the one or more processors initiate the select PIMD operation and flow moves to 718. At 718, the one or more processors set a high value of the EL indicator, informing the user that the current level of available power of the PIMD 104 is sufficient to initiate the select PIMD operation and that no further movement of the external antenna 106 is needed.

In one example, the high value and the low value of an EL indicator, informing a user whether or not there is sufficient available power for the select PIMD operation, may be implemented as two different conditions of a first type of indicator while a second type of indicator represents the degree of energy transfer between the external antenna 106 and the internal antenna 114. In a further example, the first type of indicator may be a color of an element displayed on a user interface (e.g., the color green corresponding to a high value and the color red corresponding to a low value) while the second type of indicator may be a height of the element.

Closing Statements

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that may direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications/controllers herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the units/modules/applications/controllers herein may represent circuits that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications/controllers herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A computer implemented method comprising:
    transmitting an energizing signal from an external antenna, coupled to a local external device (LED), to an implanted antenna of an implanted medical device (IMD), the energizing signal transmitted while the external antenna is at first and second positions;
    receiving, at the external antenna, first and second energy transfer characteristic (ETC) values associated with the first and second positions, respectively;
    under control of one or more processors configured with program instructions, analyzing the first and second ETC values to determine a difference therebetween;

obtaining movement data indicative of movement of the external antenna relative to a reference;

providing an energy transfer level (ETL) indicator based on the difference between the first and second ETC values, the ETL indicator providing feedback regarding a degree of energy transfer associated with at least one of the first and second positions; and changing the ETL indicator based on the difference and responsive to the movement data indicating that the external antenna moved from the first position to the second position.

2. The method of claim 1, wherein the providing the ETL indicator includes a change from a first ETL indicator associated with the first ETC value to a second ETL indicator associated with the second ETC value, the change indicating a change in the degree of energy transfer when moving the external antenna from the first position to the second position.

3. The method of claim 2, wherein the change in the degree of energy transfer represents an increase or a decrease in the degree of energy transfer, the degree of energy transfer increasing when the analyzing determines that the first ETC value is greater than the second ETC value, the degree of energy transfer decreasing when the analyzing determines that the first ETC value is less than the second ETC value.

4. The method of claim 1, wherein the first and second positions correspond to current and previous positions, respectively, of the external antenna with respect to the implanted antenna, the providing including changing the ETL indicator to indicate a decrease in the degree of energy transfer when the current position is associated with a first ETC value that is lower than the second ETC value associated with the previous position, the providing including changing the ETL indicator to indicate an increase in the degree of energy transfer when the current position is associated with a first ETC value that is greater than the second ETC value associated with the previous position.

5. The method of claim 1, wherein the IMD including an ETC monitoring unit coupled to at least one i) of an energy storage unit or ii) an AC peak detection unit, wherein the first and second ETC values are measured by the ETC monitoring unit from at least one i) of the energy storage unit or ii) the AC peak detection unit.

6. The method of claim 1, wherein the analyzing step further comprises analyzing the first and second ETC values in combination with the movement data to determine whether a change between the first and second ETC values was accompanied by movement of the external antenna.

7. The method of claim 1, wherein analyzing further comprises estimating a current level of available power of the IMD based on at least a predetermined value of power consumption of the IMD for at least one IMD operation and a change in the first ETC value over the second ETC value over a select time interval.

8. The method of claim 7, wherein estimating further comprises accounting for power calculation noise originating from moving the external antenna from the first position to the second position.

9. The method of claim 1, further comprising initiating a select IMD operation when a current level of available power of the IMD is above a threshold value for the select IMD operation.

10. The method of claim 1, further comprising delaying a select IMD operation when a current level of available power of the IMD is below a threshold value for the select IMD operation.

11. The method of claim 1, further comprising receiving third and fourth ETC values and maintaining the ETL indicator constant responsive to the movement data indicating that the external antenna did not move between the third and fourth ETC values.

12. A system comprising:

an external antenna coupled to a local external device (LED), the external antenna configured to transmit an energizing signal to an implanted antenna of an implanted medical device (IMD), the energizing signal transmitted while the external antenna is at first and second positions, and receiving first and second energy transfer characteristic (ETC) values associated with the first and second positions;

a movement detection module configured to obtain movement data indicative of movement of the external antenna relative to a reference;

at least one LED processor; and a LED memory coupled to the at least one LED processor, wherein the memory stores program instructions, wherein the program instructions are executable by the at least one processor for:

analyzing the first and second ETC values to determine a difference therebetween;

providing an energy transfer level (ETL) indicator based on the difference between the first and second ETC values, the ETL indicator providing feedback regarding a degree of energy transfer associated with at least one of the first and second positions; and changing the ETL indicator based on the difference and responsive to the movement data indicating that the external antenna moved from the first position to the second position.

13. The system of claim 12, wherein the at least one processor is configured to change the ETL indicator from a first ETL indicator associated with the first ETC value to a second ETL indicator associated with the second ETC value, the change indicating a change in the degree of energy transfer when moving the external antenna from the first position to the second position.

14. The system of claim 13, wherein the at least one processor is configured to indicate whether the change in the degree of energy transfer represents an increase or a decrease in the degree of energy transfer, the degree of energy transfer increasing when the analyzing determines that the first ETC value is greater than the second ETC value, the degree of energy transfer decreasing when the analyzing determines that the first ETC value is less than the second ETC value.

15. The system of claim 12, wherein the first and second positions correspond to current and previous positions, respectively, of the external antenna with respect to the implanted antenna; and wherein the at least one processor is configured to change the ETL indicator to indicate a decrease in the degree of energy transfer when the current position is associated with a first ETC value that is lower than the second ETC value associated with the previous position and the at least one processor is configured to change the ETL indicator to indicate an increase in the degree of energy transfer when the current position is associated with a first ETC value that is greater than the second ETC value associated with the previous position.

16. The system of claim 12, wherein the IMD includes an ETC monitoring unit coupled to at least one i) of an energy storage unit or ii) an AC peak detection unit, wherein the first and second ETC values are measured by the ETC monitoring unit from at least one i) of the energy storage unit or ii) the AC peak detection unit.

17. The system of claim 12, wherein the at least one processor is configured to analyze the first and second ETC values in combination with the movement data to determine whether a change between the first and second ETC values was accompanied by movement of the external antenna.

18. The system of claim 12, wherein the at least one processor is configured to estimate a current level of available power of the PIMD based on at least a predetermined value of power consumption of the PIMD for at least one PIMD operation and a change in the first ETC value over the second ETC value over a select time interval.

19. The system of claim 12, wherein the at least one processor is configured to account for power calculation noise originating from moving the external antenna from the first position to the second position.

20. The system of claim 12, wherein the at least one processor is configured to transmit instructions to the PIMD to initiate a select PIMD operation when a current level of available power of the PIMD is above a threshold value for the select PIMD operation.

21. The system of claim 12, wherein the at least one processor is configured to delay a select PIMD operation when a current level of available power of the PIMD is below a threshold value for the select PIMD operation.

22. The system of claim 12, wherein the external antenna is further configured to receive third and fourth ETC values and the at least one processor is further configured to maintain the ETL indicator constant responsive to the movement data indicating that the external antenna did not move between the third and fourth ETC values.

\* \* \* \* \*